US008953866B2

(12) United States Patent
George et al.

(10) Patent No.: US 8,953,866 B2
(45) Date of Patent: *Feb. 10, 2015

(54) METHOD FOR IMAGING AND DIFFERENTIAL ANALYSIS OF CELLS

(75) Inventors: Thaddeus C. George, Seattle, WA (US); David A. Basiji, Seattle, WA (US); Brian E. Hall, Seattle, WA (US); William E. Ortyn, Bainbridge Island, WA (US); Michael J. Seo, Westport, CT (US); Philip J. Morrissey, Bellevue, WA (US); Cathleen A. Zimmerman, Bainbridge Island, WA (US)

(73) Assignee: Amnis Corporation, Seattle, WA (US)

( * ) Notice: Subject to any disclaimer, the term of this patent is extended or adjusted under 35 U.S.C. 154(b) by 422 days.

This patent is subject to a terminal disclaimer.

(21) Appl. No.: 13/460,682

(22) Filed: Apr. 30, 2012

(65) Prior Publication Data

US 2012/0328177 A1  Dec. 27, 2012

Related U.S. Application Data

(63) Continuation-in-part of application No. 13/302,941, filed on Nov. 22, 2011, now Pat. No. 8,571,294, which is a continuation of application No. 13/191,270, filed on Jul. 26, 2011, now Pat. No. 8,175,371, which is a (Continued)

(51) Int. Cl.
*G06K 9/00* (2006.01)
*G01N 21/53* (2006.01)
(Continued)

(52) U.S. Cl.
CPC .............. *G01N 21/53* (2013.01); *G01N 21/645* (2013.01); *G01N 15/14* (2013.01); *G01N 21/6428* (2013.01); *G01N 15/1475* (2013.01);

(Continued)

(58) Field of Classification Search
None
See application file for complete search history.

(56) References Cited

U.S. PATENT DOCUMENTS 3,497,690 A   2/1970  Bahr et al.
3,555,280 A   1/1971  Richards, Jr.

(Continued)

FOREIGN PATENT DOCUMENTS

EP    0 154 404    9/1985
EP    0 280 559    8/1988

(Continued)

OTHER PUBLICATIONS

Henery et al. "Quantitative image based apoptotic index measurement using multispectral imaging flow cytometry: a comparison with standard photometric methods", Aug. 2008, Springer—Apoptosis, vol. 13, Issue 8, pp. 1054-1063.*

(Continued)

*Primary Examiner* — Matthew Bella
*Assistant Examiner* — Jason Heidemann
(74) *Attorney, Agent, or Firm* — Lee & Hayes, PLLC

(57) ABSTRACT

Provided are methods for determining and analyzing photometric and morphometric features of small objects, such as cells to, for example, identify different cell states. In particularly, methods are provided for identifying apoptotic cells, and for distinguishing between cells undergoing apoptosis versus necrosis.

15 Claims, 8 Drawing Sheets

Related U.S. Application Data continuation of application No. 10/593,016, filed as application No. PCT/US2005/008870 on Mar. 16, 2005, now Pat. No. 8,103,080.

(60) Provisional application No. 60/553,502, filed on Mar. 16, 2004.

(51) Int. Cl.
    *G01N 21/64*     (2006.01)
    *G01N 15/14*     (2006.01)

(52) U.S. Cl.
    CPC .... *G01N21/6456* (2013.01); *G01N 2021/6423* (2013.01); *G01N 2021/6439* (2013.01); *G01N 2021/6482* (2013.01)
    USPC ........... 382/133; 382/128; 382/181; 382/190; 382/209; 382/224; 356/300; 356/327; 356/338; 435/4; 436/164; 436/171; 436/172; 436/63; 702/19; 702/21

(56) References Cited

U.S. PATENT DOCUMENTS

| | | |
|---|---|---|
| 3,586,760 A | 6/1971 | Dillenburger |
| 3,922,069 A | 11/1975 | Kishikawa et al. |
| 4,313,734 A | 2/1982 | Leuvering |
| 4,414,575 A | 11/1983 | Yamamoto et al. |
| 4,635,293 A | 1/1987 | Watanabe |
| 4,662,742 A | 5/1987 | Chupp |
| 4,677,680 A | 6/1987 | Harima et al. |
| 4,703,017 A | 10/1987 | Campbell et al. |
| 4,737,932 A | 4/1988 | Baba |
| 4,770,992 A | 9/1988 | Van den Engh et al. |
| 4,777,525 A | 10/1988 | Preston, Jr. |
| 4,786,165 A | 11/1988 | Yamamoto et al. |
| 4,845,197 A | 7/1989 | Petersen et al. |
| 4,857,453 A | 8/1989 | Ullman et al. |
| 5,096,807 A | 3/1992 | Leaback |
| 5,107,522 A | 4/1992 | Kitayama et al. |
| 5,122,453 A | 6/1992 | Martin et al. |
| 5,141,609 A | 8/1992 | Sweedler et al. |
| 5,153,916 A | 10/1992 | Inagaki et al. |
| 5,159,397 A | 10/1992 | Kosaka et al. |
| 5,159,398 A | 10/1992 | Maekawa et al. |
| 5,159,642 A | 10/1992 | Kosaka |
| 5,247,339 A | 9/1993 | Ogino |
| 5,247,340 A | 9/1993 | Ogino |
| 5,257,182 A | 10/1993 | Luck et al. |
| 5,272,354 A | 12/1993 | Kosaka |
| 5,351,311 A | 9/1994 | Rogers et al. |
| 5,372,936 A | 12/1994 | Fraatz et al. |
| 5,422,712 A | 6/1995 | Ogino |
| 5,436,144 A | 7/1995 | Stewart et al. |
| 5,444,527 A | 8/1995 | Kosaka |
| 5,459,240 A | 10/1995 | Foxwell et al. |
| 5,471,294 A | 11/1995 | Ogino |
| 5,526,258 A | 6/1996 | Bacus |
| 5,547,849 A | 8/1996 | Baer et al. |
| 5,548,349 A | 8/1996 | Mizuguchi et al. |
| 5,548,395 A | 8/1996 | Kosaka |
| 5,568,315 A | 10/1996 | Shuman |
| 5,596,401 A | 1/1997 | Kusuzawa |
| 5,621,460 A | 4/1997 | Hatlestad et al. |
| 5,625,048 A | 4/1997 | Tsien et al. |
| 5,633,503 A | 5/1997 | Kosaka |
| 5,644,388 A | 7/1997 | Maekawa et al. |
| 5,674,743 A | 10/1997 | Ulmer |
| 5,686,960 A | 11/1997 | Sussman et al. |
| 5,695,934 A | 12/1997 | Brenner |
| 5,732,150 A * | 3/1998 | Zhou et al. .................... 382/133 |
| 5,733,721 A | 3/1998 | Hemstreet, III et al. |
| 5,754,291 A | 5/1998 | Kain |
| 5,760,899 A | 6/1998 | Eismann |
| 5,764,792 A | 6/1998 | Kennealy |
| 5,784,162 A | 7/1998 | Cabib et al. |
| RE35,868 E | 8/1998 | Kosaka |
| 5,828,776 A | 10/1998 | Lee et al. |
| 5,831,723 A | 11/1998 | Kubota et al. |
| 5,844,670 A | 12/1998 | Morita et al. |
| 5,848,123 A | 12/1998 | Strommer |
| 5,855,753 A | 1/1999 | Trau et al. |
| 5,879,900 A | 3/1999 | Kim et al. |
| 5,900,942 A | 5/1999 | Spiering |
| 5,926,283 A | 7/1999 | Hopkins |
| 5,929,986 A | 7/1999 | Slater et al. |
| 5,959,953 A | 9/1999 | Alon |
| 5,985,549 A | 11/1999 | Singer et al. |
| 5,986,061 A | 11/1999 | Petska |
| 5,989,835 A | 11/1999 | Dunlay et al. |
| 6,007,994 A | 12/1999 | Ward et al. |
| 6,007,996 A | 12/1999 | McNamara et al. |
| 6,014,468 A | 1/2000 | McCarthy et al. |
| 6,066,459 A | 5/2000 | Garini et al. |
| 6,108,082 A | 8/2000 | Pettipiece et al. |
| 6,115,119 A | 9/2000 | Sieracki et al. |
| 6,116,739 A | 9/2000 | Ishihara et al. |
| 6,151,405 A * | 11/2000 | Douglass et al. .............. 382/133 |
| 6,156,465 A | 12/2000 | Cao et al. |
| 6,159,686 A | 12/2000 | Kardos et al. |
| 6,165,734 A | 12/2000 | Garini et al. |
| 6,210,973 B1 | 4/2001 | Pettit |
| 6,211,955 B1 | 4/2001 | Basiji et al. |
| 6,221,596 B1 * | 4/2001 | Yemini et al. ................. 435/6.12 |
| 6,229,913 B1 | 5/2001 | Nayar et al. |
| 6,249,314 B1 | 6/2001 | Yamamoto et al. |
| 6,249,341 B1 | 6/2001 | Basiji et al. |
| 6,256,096 B1 | 7/2001 | Johnson |
| 6,259,807 B1 | 7/2001 | Ravkin |
| 6,330,081 B1 | 12/2001 | Scholten |
| 6,330,361 B1 | 12/2001 | Mitchell et al. |
| 6,381,363 B1 | 4/2002 | Muching et al. |
| 6,473,176 B2 | 10/2002 | Basiji et al. |
| 6,507,391 B2 | 1/2003 | Riley et al. |
| 6,510,319 B2 | 1/2003 | Baum et al. |
| 6,519,355 B2 | 2/2003 | Nelson |
| 6,522,781 B1 | 2/2003 | Norikane et al. |
| 6,532,061 B2 | 3/2003 | Ortyn et al. |
| 6,548,259 B2 | 4/2003 | Ward et al. |
| 6,549,664 B1 | 4/2003 | Daiber et al. |
| 6,563,583 B2 | 5/2003 | Ortyn et al. |
| 6,580,504 B1 | 6/2003 | Basiji et al. |
| 6,583,865 B2 | 6/2003 | Basiji et al. |
| 6,608,680 B2 | 8/2003 | Basiji et al. |
| 6,608,682 B2 | 8/2003 | Ortyn et al. |
| 6,618,140 B2 | 9/2003 | Frost et al. |
| 6,620,591 B1 | 9/2003 | Dunlay et al. |
| 6,671,044 B2 | 12/2003 | Ortyn et al. |
| 6,671,624 B1 | 12/2003 | Dunlay et al. |
| 6,707,551 B2 | 3/2004 | Ortyn et al. |
| 6,716,588 B2 | 4/2004 | Sammak et al. |
| 6,727,066 B2 | 4/2004 | Kaser |
| 6,743,576 B1 | 6/2004 | Sabry et al. |
| 6,763,149 B2 | 7/2004 | Riley et al. |
| 6,778,263 B2 | 8/2004 | Ortyn et al. |
| 6,873,733 B2 | 3/2005 | Dowski, Jr. |
| 6,875,973 B2 | 4/2005 | Ortyn et al. |
| 6,906,792 B2 | 6/2005 | Ortyn et al. |
| 6,927,922 B2 | 8/2005 | George et al. |
| 6,934,408 B2 | 8/2005 | Frost et al. |
| 6,947,128 B2 | 9/2005 | Basiji et al. |
| 6,947,136 B2 | 9/2005 | Ortyn et al. |
| 6,975,400 B2 | 12/2005 | Ortyn et al. |
| 7,006,710 B2 | 2/2006 | Riley et al. |
| 7,042,639 B1 | 5/2006 | McDowell |
| 7,079,708 B2 | 7/2006 | Riley et al. |
| 7,087,877 B2 | 8/2006 | Ortyn et al. |
| 7,180,673 B2 | 2/2007 | Dowski, Jr. |
| 7,190,832 B2 | 3/2007 | Frost et al. |
| 7,221,457 B2 | 5/2007 | Jorgenson et al. |
| 7,315,357 B2 | 1/2008 | Ortyn et al. |
| 7,450,229 B2 | 11/2008 | Ortyn et al. |
| 7,667,761 B2 | 2/2010 | Thomas |
| 7,817,840 B2 | 10/2010 | Mattheakis et al. |

(56) References Cited

U.S. PATENT DOCUMENTS

| | | | |
|---|---|---|---|
| 8,103,080 B2 | 1/2012 | George et al. | |
| 8,175,371 B2 | 5/2012 | George et al. | |
| 2001/0006416 A1 | 7/2001 | Johnson | |
| 2001/0012620 A1 | 8/2001 | Rich | |
| 2002/0028471 A1* | 3/2002 | Oberhardt | 435/7.21 |
| 2002/0071121 A1 | 6/2002 | Ortyn et al. | |
| 2002/0119441 A1* | 8/2002 | Elias | 435/4 |
| 2002/0126275 A1 | 9/2002 | Johnson | |
| 2002/0142304 A1* | 10/2002 | Anderson et al. | 435/6 |
| 2002/0146734 A1 | 10/2002 | Ortyn et al. | |
| 2002/0154798 A1 | 10/2002 | Cong et al. | |
| 2002/0159625 A1* | 10/2002 | Elling | 382/133 |
| 2002/0164063 A1 | 11/2002 | Heckman | |
| 2002/0172987 A1* | 11/2002 | Terstappen et al. | 435/7.23 |
| 2003/0040031 A1 | 2/2003 | Kim et al. | |
| 2003/0048931 A1 | 3/2003 | Johnson et al. | |
| 2003/0049701 A1 | 3/2003 | Muraca | |
| 2003/0059093 A1 | 3/2003 | Rosania et al. | |
| 2003/0059764 A1* | 3/2003 | Ravkin et al. | 435/4 |
| 2003/0096322 A1 | 5/2003 | Giuliano et al. | |
| 2003/0103662 A1 | 6/2003 | Finkbeiner | |
| 2003/0104439 A1 | 6/2003 | Finch | |
| 2003/0202689 A1 | 10/2003 | Hansen et al. | |
| 2004/0021868 A1 | 2/2004 | Ortyn et al. | |
| 2004/0029213 A1 | 2/2004 | Callahan et al. | |
| 2004/0093166 A1 | 5/2004 | Kil | |
| 2004/0111220 A1 | 6/2004 | Ochs et al. | |
| 2004/0218184 A1 | 11/2004 | Jorgenson et al. | |
| 2004/0241759 A1 | 12/2004 | Tozer et al. | |
| 2005/0014129 A1 | 1/2005 | Cliffel et al. | |
| 2005/0094147 A1 | 5/2005 | Yaroslavsky et al. | |
| 2006/0029267 A1 | 2/2006 | Frost et al. | |
| 2006/0040305 A1 | 2/2006 | Fejgin et al. | |
| 2006/0246481 A1 | 11/2006 | Finch et al. | |
| 2006/0257884 A1 | 11/2006 | Brawley et al. | |
| 2007/0020697 A1* | 1/2007 | Cualing et al. | 435/7.2 |
| 2007/0054350 A1 | 3/2007 | Walker | |
| 2007/0146873 A1* | 6/2007 | Ortyn et al. | 359/386 |
| 2008/0240539 A1 | 10/2008 | George et al. | |
| 2009/0202130 A1 | 8/2009 | George et al. | |
| 2011/0280467 A1 | 11/2011 | George et al. | |
| 2012/0100532 A1 | 4/2012 | George et al. | |

FOREIGN PATENT DOCUMENTS

| | | |
|---|---|---|
| EP | 0 281 327 | 6/1993 |
| EP | 0 372 707 | 3/1996 |
| EP | 0 950 890 | 10/1999 |
| EP | 1 316 793 | 6/2003 |
| WO | WO 88/08534 | 11/1988 |
| WO | WO 90/10715 | 9/1990 |
| WO | WO 95/20148 | 7/1995 |
| WO | WO 97/26333 | 7/1997 |
| WO | WO 98/53093 | 11/1998 |
| WO | WO 98/53300 | 11/1998 |
| WO | WO 99/24458 | 5/1999 |
| WO | WO 99/64592 | 12/1999 |
| WO | WO 00/06989 | 2/2000 |
| WO | WO 00/14545 | 3/2000 |
| WO | WO 00/42412 | 7/2000 |
| WO | WO 01/11341 | 2/2001 |
| WO | WO 01/46675 | 6/2001 |
| WO | WO 02/17622 | 2/2002 |
| WO | WO 02/18537 | 3/2002 |
| WO | WO 02/31182 | 4/2002 |
| WO | WO 02/35474 | 5/2002 |
| WO | WO 02/073200 | 9/2002 |
| WO | WO 02/079391 | 10/2002 |
| WO | WO 2005/090945 | 9/2005 |
| WO | WO2005090945 A1 | 9/2005 |
| WO | WO 2005/098430 | 10/2005 |

OTHER PUBLICATIONS

Young et al. "Towards automatic cell identification in DIC microscopy", Nov. 1998, Journal of Microscopy, vol. 192, Pt 2, pp. 186-193.

Nicoletti et al. "Common Methods for Measuring Apoptotic Cell Death by Flow Cytometry", 1997, The Purdue Cytometry CD-ROM vol. 3, Purdue University, West Lafayette, ISBN 1-890473-02-2.

Vitale et al. "Apoptosis vs. Necrosis", The Purdue Cytometry CD-ROM vol. 4, Publisher. Purdue University Cytometry Laboratories, West Lafayette, IN, ISBN 1-890473-03-0, hereinafter Vitale.

Vermes et al. "Flow cytometry of apoptotic cell death", Journal of Immunological Methods 243 (2000) 167-190, examiner refers applicant to abstract, fig. 1, and p. 182.

Amann et al., "Fluorescent-Oligonucleotide Probing of Whole Cells for Determinative, Phylogenetic, and Environmental Studies in Microbiology," Journal of Bacteriology vol. 172, No. 2: 762-770, Feb. 1990.

Arkesteijn et al., "Chromosome Specific DNA Hybridization in Suspension for Flow Cytometric Detection of Chimerism in Bone Marrow Transplantation and Leukemia," Cytometry 19: 353-360, Apr. 1995.

Bains et al., "Flow Cytometric Quantitation of Sequence-Specific mRNA in Hemopoietic Cell Suspension by Primer-Induced in Situ (PRINS) Fluorescent Nucleotide Labeling," Experimental Cell Research 208: 321-326, Sep. 1993.

Barren, III et al., "Method for Identifying Prostate Cells in Semen Using Flow Cytometry," The Prostate 36: 181-188, Aug. 1998.

Bauman et al., "Flow Cytometric Detection of Ribosomal RNA in Suspended Cells by Fluorescent in Situ Hybridization," Cytometry 9: 517-524, Nov. 1998.

Baumgartner et al., "Automated Evaluation of Frequencies of Aneuploid Sperm by Laser-Scanning Cytometry (LSC)," Cytometry 44: 156-160, Jun. 2001.

Ben-Eliezer et al., "All-optical extended depth of field imaging system," Journal of Optics A: Pure and Applied Optics 5: SI64-S169, Sep. 2003.

Biggs et al., "Acceleration of iterative image restoration algorithms" Applied Optics vol. 36, No. 8: 1766-1775, Mar. 10, 1997.

Boyle et al., "Isolation and Initial Characterization of a Large Repeat Sequence Element Specific to Mouse Chromosome 8," Genomics vol. 12, No. 3: 517-525, Mar. 1992.

Callet-Bauchu et al., "Distribution of the cytogenetic abnormality +i(3)(q10) in persistent polyclonal B-cell lymphocytosis: a FICTION study in three cases," British Journal of Haematology 99: 531-536, Dec. 1997.

Ding et al., "Characterization and Quantitation of NF-κB Nuclear Translocation Induced by Interleukin-1 and Tumor Necrosis Factor-α," The Journal of Biological Chemistry vol. 273, No. 44: 28897-28905, Oct. 30, 1998.

Disteche et al., "Isolation and characterization of two repetitive DNA fragments located near the centromere of the mouse X chromosome," Cytogenetics and Cell Genetics 39: 262-268, 1985.

Dragowska et al., "Measurement of DNA repeat sequence by flow cytometry," Cytometry Supplement 7: 51, Oct. 1994.

Engvall, Eva. "Enzyme Immunoassay ELISA and EMIT," Methods in Enzymology vol. 70, Part A: 419-439, Dec. 1980.

Fernandez-Lago et al., "Fluorescent Whole-Cell Hybridization with 16S rRNA-Targeted Oligonucleotide Probes To Identify *Brucella* spp. by Flow Cytometry," Journal of Clinical Microbiology vol. 38, No. 7: 2768-2771, Jul. 2000.

George et al., "Extended depth of field using a logarithmic asphere" Journal of Optics A: Pure and Applied Optics 5: S157-S163, Sep. 2003.

George et al., "Distinguishing Modes of Cell Death Using the ImageStream® Multispectral Imaging Flow Cytometer," Cytometry Part A 59A: 237-245, Jun. 2004.

George et al., "Quantitative measurement of nuclear translocation events using similarity analysis of multispectral cellular images obtained in flow," Journal of Immunological Methods 311: 117-129, Apr. 2006.

Gordy et al., "Visualization of Antigen Presentation by Actin-Mediated Targeting of Glycolipid-Enriched Membrane Domains to the Immune Synapse of B cell APCs." Journal of Immunology vol. 172, No. 4: 2030-2038, Feb. 15, 2004.

Hecht, Eugene. "Optics 4th ed." Addison-Wesley Longman, Inc., XP-002465391, ISBN: 0-8053-8566-5, 2002.

(56) References Cited

OTHER PUBLICATIONS

Hultdin et al., "Telomere analysis by fluorescence in situ hybridization and flow cytometry," Nucleic Acids Research vol. 26, No. 16: 3651-3656, Aug. 15, 1998.
Kubota et al., "Flow Cytometer and Imaging Device Used in Combination." Cytometry 21: 129 132, Oct. 1995.
Kubota, Fumio. "Analysis of red cell and platelet morphology using an imaging combined flow cytometer." Clin. Lab. Haem. 25: 71-76, Apr. 2003.
Lauzon et al., "Flow Cytometric Measurement of Telomere Length," Cytometry 42: 159-164, Jun. 2000.
Levron et al., "Sperm chromosome abnormalities in men with severe male factor infertility who are undergoing in vitro fertilization with intracytoplasmic sperm injection," Fertility and Sterility vol. 76, No. 3: 479-484, Sep. 2001.
Lowe et al., "Aneuploid epididymal sperm detected in chromosomally normal and Robertsonian translocation-bearing mice using a new three-chromosome FISH method," Chromosoma 105: 204-210, 1996.
Majno et al., "Apoptosis, Oncosis, and Necrosis An Overview of Cell Death," American Journal of Pathology vol. 146, No. 1: 3-15, Jan. 1, 1995.
Martin et al., "Detection of aneuploidy in human interphase spermatozoa by fluorescence in situ hybridization (FISH)," Cytogenetics and Cell Genetics 64: 23-26, 1993.
Nautiyal et al., "17β-Estradiol induces nuclear translocation of CrkL at the window of embryo implantation," Biochemical and Biophysical Research Communications 318: 103-112, 2004.
Ong, Sim Heng, "Development of a System for Imaging and Classifying Biological Cells in a Flow Cytometer," Doctor of Philosophy Thesis, University of Sydney, School of Electrical Engineering, Aug. 1985.
Ong et al., "Development of an Image Flow Cytometer," Analytical and Quantitative Cytology and Histology. XIVth International Conference on Medical and Biological Engineering and the VIIth International Conference on Medical Physics, Finland: 375-382, Aug. 1987.
Ong et al., "Optical Design in a Flow System for Imaging Cells," Sciences in Medicine, vol. 14, No. 2: 74 80, Jun. 1991.
Ong et al., "Analysis of MTF Degradation in the Imaging of Cells in a Flow System," International Journal of Imaging Systems & Technology 5: 243 250, Autum(Fall) 1994.
Ortyn et al., "Extended Depth of Field Imaging for High Speed Cell Analysis" Cytometry Part A 71A: 215-231, Apr. 2007.
Pala et al., "Flow cytometric measurement of intracellular cytokines," Journal of Immunological Methods 243: 107-124, Mar. 2000.
Pang et al., "Detection of aneuploidy for chromosomes 4, 6, 7, 8, 9, 10, 11, 12, 13, 17, 18, 21, X and Y by fluorescence in-situ hybridization in spermatozoa from nine patients with oligoasthenoteratozoospermia undergoing intracytoplasmic sperm injection," Human Reproduction vol. 14, No. 5: 1266-1273, May 1999.
Patterson et al., "Detection of HIV-1 DNA and Messenger RNA in Individual Cells by PCR-Driven in Situ Hybridization and Flow Cytometry," Science 260: 976-979, May 14, 1993.
Perreault et al., "The Role of Disulfide Bond Reduction during Mammalian Sperm Nuclear Decondensation in Vivo," Developmental Biology 101: 160-167, Jan. 1984.
Pinkel et al., "Cytogenetic analysis using quantitative, high sensitivity, fluorescence hybridization," Proceedings of the National Academy of Sciences: Genetics 83: 2934-2938, May 1986.
Pollice et al., "Sequential Paraformaldehyde and Methanol Fixation for Simultaneous Flow Cytometric Analysis of DNA, Cell Surface Proteins, and Intracellular Proteins," Cytometry 13: 432-444, 1992.
Ried et al., "Simultaneous visualization of seven different DNA probes by in situ hybridization using combinatorial fluorescence and digital imaging microscopy," Proceedings of the National Academy of Sciences: Genetics 89: 1388-1392, Feb. 1992.

Robbins et al., "Aneuploidy in sperm of Hodgkin's disease patients receiving NOVP chemotherapy," the American Journal of Human Genetics vol. 55, No. 3—Supplement: A68 (371), Sep. 1994.
Robbins et al., "Detection of Aneuploid Human Sperm by Fluorescence In Situ Hybridization: Evidence for a Donor Difference in Frequency of Sperm Disomic for Chromosomes I and Y," The American Journal of Human Genetics, 52: 799-807, Apr. 1993.
Robbins et al., "Three-probe Fluorescence in situ Hybridization to Assess Chromosome X, Y, and 8 Aneuploidy in Sperm of 14 Men from Two Healthy Groups: Evidence for a Paternal Age Effect on Sperm Aneuploidy," Reproduction, Fertility and Development 7: 799-809, 1995.
Robbins et al., "Use of Fluorescence in Situ Hybridization (FISH) to Assess Effects of Smoking, Caffeine, and Alcohol on Aneuploidy Load in Sperm of Healthy Men," Environmental and Molecular Mutagenesis 30: 175-183, 1997.
Rufer et al., "Telomere length dynamics in human lymphocyte subpopulations measured by flow cytometry," Nature Biotechnology 16: 743-747, Aug. 1998.
The European Office Action mailed Jul. 10, 2013 for European Patent Application No. 05725804.8, a counterpart foreign application of US Patent No. 8,103,080, 8 pages.
The Extended EP Search Report mailed Jul. 15, 2013 for European patent application No. 13165742.1, 7 pages.
Salzman et al., "Light Scatter: Detection and Usage," Current Protocols in Cytometry Supplement 9: 1.13.1-1.138.8, 1999.
Satoh et al., "Small Aggregates of Platelets Can Be Detected Sensitively by a Flow Cytometer Equipped With an Imaging Device: Mechanisms of Epinephrine Induced Aggregation and Antiplatelet Effects of Beraprost." Cytometry 48: 194 201, 2002.
Schmid et al., "Evaluation of inter-scorer and inter-laboratory reliability of the mouse epididymal sperm aneuploidy (m-ESA) assay," Mutagenesis vol. 16, No. 3: 189-195, 2001.
Schmid et al., "Simultaneous Flow Cytometric Analysis of Two Cell Surface Markers, Telomere Length, and DNA Content," Cytometry 49: 96-105, 2002.
Schwerin et al., "Quantification of Y Chromosome Bearing Spermatozoa of Cattle Using in Situ Hybridization," Molecular Reproduction and Development 30: 39-43, 1991.
Shi et al., "Aneuploidy in human sperm: a review of the frequency and distribution of aneuploidy, effects of donor age and lifestyle factors," Cytogenetics and Cell Genetics 90: 219-226, 2000.
Timm et al., "Amplification and Detection of a Y-Chromosome DNA Sequence by Fluorescence In Situ Polymerase Chain Reaction and Flow Cytometry Using Cells in Suspension," Cytometry (Communications in Clinical Cytometry) 22: 250-255, 1995.
Trask et al., "Fluorescence in situ hybridization to interphase cell nuclei in suspension allows flow cytometric analysis of chromosome content and microscopic analysis of nuclear organization," Human Genetics 78:251-259, 1988.
Tucker et al., "Extended depth of field and aberration control for inexpensive digital microscope systems" Optics Express vol. 4, No. 11: 467-474, May 24, 1999.
van Dekken et al., "Flow Cytometric Quantification of Human Chromosome Specific Repetitive DNA Sequences by Single and Bicolor Fluorescent In Situ Hybridization to Lymphocyte Interphase Nuclei," Cytometry 11: 153-164, 1990.
van den Berg et al., "Detection of Y Chromosome by In situ Hybridization in Combination with Membrane Antigens by Two-Color Immunofluorescence," Laboratory Investigation vol. 64, No. 5: 623-628, 1991.
Wang et al., "A Novel Apoptosis Research Method With Imaging Combined Flow Cytometer and HITC OR IR 125 Staining," Cytometry (Clinical Cytometry) 50: 267 274, 2002.
Weber-Matthieson et al., "Rapid immunophenotypic characterization of chromosomally aberrant cells by the new FICTION method," Cytogenetics Cell Genetics 63: 123-125, 1993.
Weber-Matthieson et al., "Simultaneous Fluorescence Immunophenotyping and Interphase Cytogenetics: A Contribution to the Characterization of Tumor Cells," Journal of Histochemistry and Cytochemistry vol. 40, No. 2: 171-175, 1992.

(56) References Cited

OTHER PUBLICATIONS

Wietzorrek et al., "A New Multiparameter Flow Cytometer: Optical and Electrical Cell Analysis in Combination With Video Microscopy in Flow," Cytometry 35: 291 301, 1999.

Wyrobek et al., "Smokers produce more aneuploid sperm than non-smokers," The American Society of Human Genetics, 45th Annual Meeting, A131: 737, Oct. 24-28, 1995.

Wyrobek et al., "Detection of Sex Chromosomal Aneuploidies X-X, Y-Y, and X-Y, in Human Sperm Using Two-Chromosome Fluorescence In Situ Hybridization," American Journal of Medical Genetics 53: 1-7, 1994.

Wyrobek et al., "Fluorescence In Situ Hybridization to Y Chromosomes in Decondensed Human Sperm Nuclei," Molecular Reproduction and Development 27: 200-208, 1990.

Ferraro et al., "Extended focused image in microscopy by digital holography," Optics Express, vol. 13, No. 18: 6738-6749, Sep. 2005.

Darzynkiewicz et al, "Features of Apoptotic Cells Measured by Flow Cytometry," 1992, Cytometry 13(8), pp. 795-808.

Timm et al., "Fluorescent In Situ Hybridization En Suspension (FISHES) Using Digoxigenin-qLabeled Probes and Flow Cytometry," Biotechniques vol. 12, No. 3: 362-367, Mar. 1992.

Non-Final Office for U.S. Appl. No. 13/302,941, mailed on Mar. 29, 2013, Thaddeus C. George et al., "Method for Imaging and Differential Analysis of Cells ", 14 pages.

Office Action for U.S. Appl. No. 13/802,328, mailed on Jun. 19, 2014, George et al., "Method for Imaging and Differential Analysis of Cells", 17 pages.

\* cited by examiner

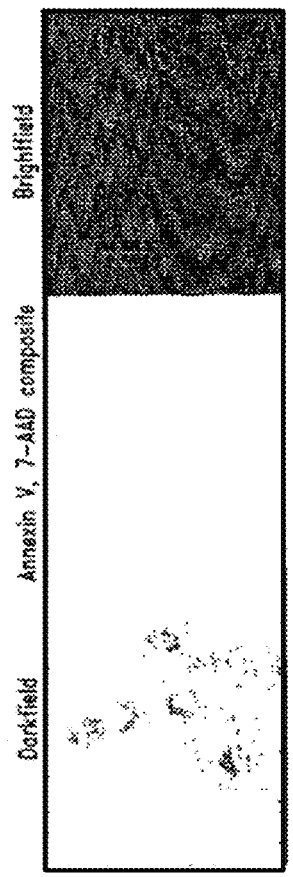 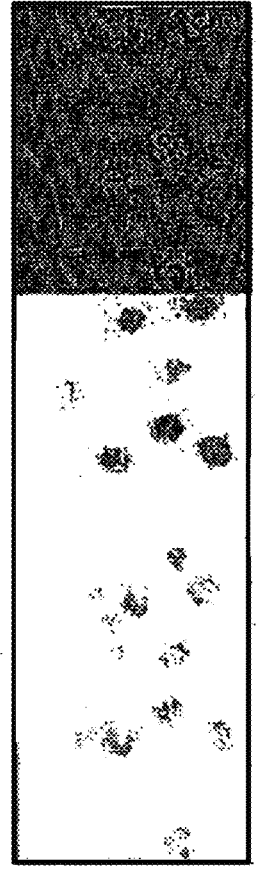 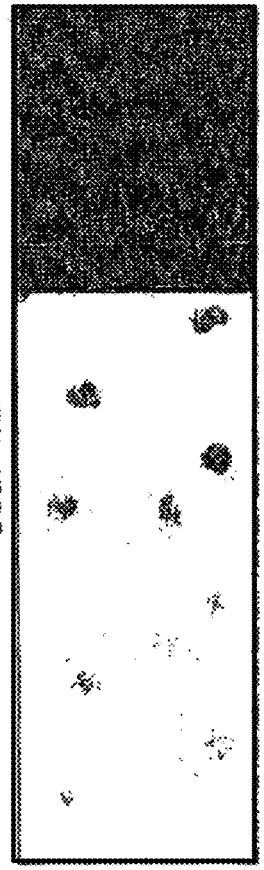
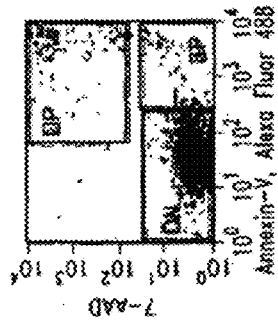 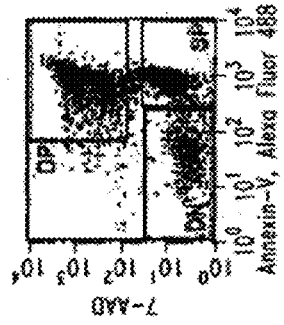 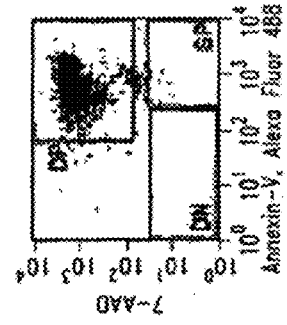
FIG. 2A  FIG. 2B  FIG. 2C

METHOD FOR IMAGING AND DIFFERENTIAL ANALYSIS OF CELLS

RELATED APPLICATIONS

This application is a continuation-in-part of copending patent application Ser. No. 13/302,941, filed on Nov. 22, 2011, which is a continuation of a copending patent application Ser. No. 13/191,270, filed on Jul. 26, 2011, which is a continuation of copending patent application Ser. No. 10/593,016, filed on Sep. 14, 2006, the benefit of the filing dates of which are hereby claimed under 35 U.S.C. §120. Patent application Ser. No. 10/593,016 is a National Stage application based on a prior PCT application, PCT/US05/008870, filed on Mar. 16, 2005, the benefit of the filing date of which is hereby claimed under 35 U.S.C. §371. PCT/US05/008870 itself is based on a prior provisional application Ser. No. 60/553,502, filed on Mar. 16, 2004, the benefit of the filing date of which is hereby claimed under 35 U.S.C. §119(e).

FIELD OF THE INVENTION

The present disclosure relates generally to imaging small moving objects or particles to analyze and distinguish such objects, and more specifically, to a system and method for determining and analyzing photometric and morphometric features of small objects, such as cells to, for example, identify different cell states.

DESCRIPTION OF THE RELATED ART

Apoptosis is a complex, tightly regulated process by which a cell orchestrates its own destruction in response to specific internal or external triggers (Jacobson et al., Cell 88:347, 1997; Rathmell and Thompson, Cell 109 (Supp):S97, 2002), and proceeds in a manner that is designed to prevent damage to surrounding cells and tissues. Apoptotic cells typically appear shrunken, with condensed chromatin and fragmented nuclei. Although plasma membrane integrity is initially preserved, in later stages the plasma membrane becomes compromised and the cells shed apoptotic bodies consisting of organelles, cytoplasm and/or nuclear fragments. Apoptotic cells are rapidly phagocytosed and eliminated in vivo, thus preventing the induction of inflammatory responses, which is a process critical to the maintenance of tissue and immune cell development and homeostasis (Jacobson et al.; Rathmell and Thompson; Vaux and Korsmeyer, Cell 96:245, 1999). Inappropriately low apoptotic rates can result in cancer or autoimmune disease, while high rates can result in neurodegenerative disease or immunodeficiency (Ashkenazi and Dixit, Science 281:1305, 1998; Thompson, Science 267:1456, 1995; Fadeel et al., Leukemia 14:1514, 2000). In contrast, necrotic cell death is a largely unregulated process in which the cells generally have intact nuclei with limited chromatin condensation. Cells undergoing necrosis do not induce an early phagocytic response. Instead, the cells swell and rupture, and the release of cellular contents can result in significant local tissue damage and inflammation (Jacobson et al.).

Research aimed at cell death regulation has produced a number of methods to identify and quantify apoptotic cells, and to distinguish between cells undergoing apoptosis versus necrosis. Among these, flow cytometry has become a commonly used tool in the identification and quantification of apoptosis. Changes in cell size, shape, and granularity associated with apoptosis can be inferred from scattered laser light (Ormerod et al., J. Immunol. Methods 153:57, 1992). Early intracellular events, such as the loss of the mitochondrial inner membrane potential or activation and cleavage of caspases, can also be detected using electro-potential sensitive dyes (Castedo et al., J. Immunol. Methods 265:39, 2002; Green and Kroemer, Trends Cell Biol. 8:267, 1998; Green and Reed, Science 281:1309, 1998; Kroemer and Reed, Nat. Med. 6:513, 2000; Lizard et al., Cytometry 21:275, 1995) or fluorogenic substrates (Komoriya et al., J. Exp. Med. 191:1819, 2000; Smolewski et al., J. Immunol. Methods 265:111, 2002; Lecoeur et al., J. Immunol. Methods 265:81, 2002). Another early apoptotic event results in exposure of phosphatidylserine on the outer surface of the plasma membrane, which can be detected by fluorochrome-labeled annexin V (van Engeland et al., Cytometry 31:1, 1998; Vermes et al., J. Immunol. Methods 184:39, 1995; Koopman et al., Blood 84:1415, 1994; Verhoven et al., J. Exp. Med. 182:1597, 1995). Apoptotic cells eventually lose the ability to exclude cationic nucleotide-binding dyes and nuclear DNA stains with dyes, such as propidium iodide and 7-aminoactinomycin D (7-AAD) (Lecoeur et al., 2002; Gaforio et al., Cytometry 49:8, 2002; Ormerod et al., Cytometry 14:595, 1993; Schmid et al., J. Immunol. Methods 170:145, 1994; Philpott et al., Blood 87:2244, 1996). Other techniques that can be used to identify apoptosis include biochemical identification of the activated proteases (e.g., caspases, PARP), release of mitochondrial cytochrome c, quantification of cellular DNA content, and progressive endonucleolytic cleavage of nuclear DNA (Alnemri et al., Cell 87:171, 1996; Kohler et al., J. Immunol. Methods 265:97, 2002; Gong et al., Anal. Biochem. 218:314, 1994; Gorczyca et al., Leukemia 7:659, 1993; Gorczyca et al., Cancer Res. 53:1945, 1993).

As noted above, conventional flow cytometric methods do not provide direct morphologic evidence of cell death. Indeed, these techniques usually target molecular changes that are associated with apoptosis, but such changes are not always specific to apoptosis and may also be present in cells undergoing necrotic death (Lecoeur et al., 2002; Lecoeur et al., Cytometry 44:65, 2001; Kerr et al., Br. J. Cancer 26:239, 1972). For example, necrotic cells, like advanced (late-stage) apoptotic cells, stain with both annexin V and 7-AAD (Lecoeur et al., 2002; Lecoeur et al., 2001). Thus, visualization of the characteristic morphologic changes associated with apoptosis is still considered to be absolutely necessary for its identification (Jacobson et al.; Darzynkiewicz et al. Cytometry 27:1, 1997). Standard microscopic techniques allow visualization of specific molecular and biochemical changes associated with apoptosis and also morphologic changes that distinguish apoptosis from necrosis. However, these standard techniques also require subjective analysis and time-consuming image viewing, which only allows for processing of relatively limited numbers of cells and, therefore, makes it difficult to attain statistically valid comparisons (Tarnok and Gerstner, Cytometry 50:133, 2002).

Thus, the need exists for techniques that can provide the statistical power offered by flow cytometry coupled with the objective assessment capabilities associated with microscopic analysis. For example, interest in the dynamic nature of the living cell and efforts to model cell processes (variously termed "cytomics" or "systems biology") are powerful drivers for new techniques to acquire ever more comprehensive data from cells and cell populations.

BRIEF DESCRIPTION OF THE DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIGS. 2A-2C show an analysis of cell death using standard flow cytometry and immunofluorescence microscopy. Untreated Jurkat cells (A), Jurkat cells treated with 1 .mu.M CPT for 18 hrs (B), and Jurkat cells treated with 0.3% hydrogen peroxide for 1 hour (C) were stained with Alexa Fluor 488 conjugated annexin V and 7-AAD. Cells were analyzed either by conventional flow cytometry (using a BD FACSort™) or visualized on slides using a Nikon Eclipse E600 fluorescence microscope equipped with bandpass filters appropriate for Alexa Fluor 488 (535/40 nm) and 7-AAD (630/60 nm) fluorescence. The 2-color dot-plots of annexin V vs. 7-AAD, and the brightfield, combined fluorescence and darkfield microscopic images are shown.

DESCRIPTION

The instant disclosure relates to the use of both photometric and morphometric features derived from multi-mode imagery of objects (e.g., cells) in flow to discriminate cell states or types, and cell features, in heterogeneous populations of cells, including both non-adherent and adherent cell types. A surprising result of the instant disclosure is the ability to discriminate between different cell states, such as differentiating and identifying live cells, necrotic cells, and cells in both the early and late stages of apoptosis, by using unique combinations of features provided in the ImageStream™ Multispectral Imaging Cytometer and the IDEAS™ data analysis software. Discussed in more detail below are single-step methods for basic and complex morphometric classification of objects in flow, which may be combined with comprehensive multispectral imagery and photometric features to allow, for example, the identification of different cell features and/or cell types or states not feasible with standard flow cytometry.

In the present description, any concentration range, percentage range, or integer range is to be understood to include the value of any integer within the recited range and, when appropriate, fractions thereof (such as one tenth and one hundredth of an integer, etc.), unless otherwise indicated. As used herein, the term "about" means±15%. As used herein, the use of an indefinite article, such as "a" or "an", should be understood to refer to the singular and the plural of a noun or noun phrase (i.e., meaning "one or more" of the enumerated elements or components). The use of the alternative (e.g., "or") should be understood to mean either one, both or any combination thereof of the alternatives.

Figure 1:
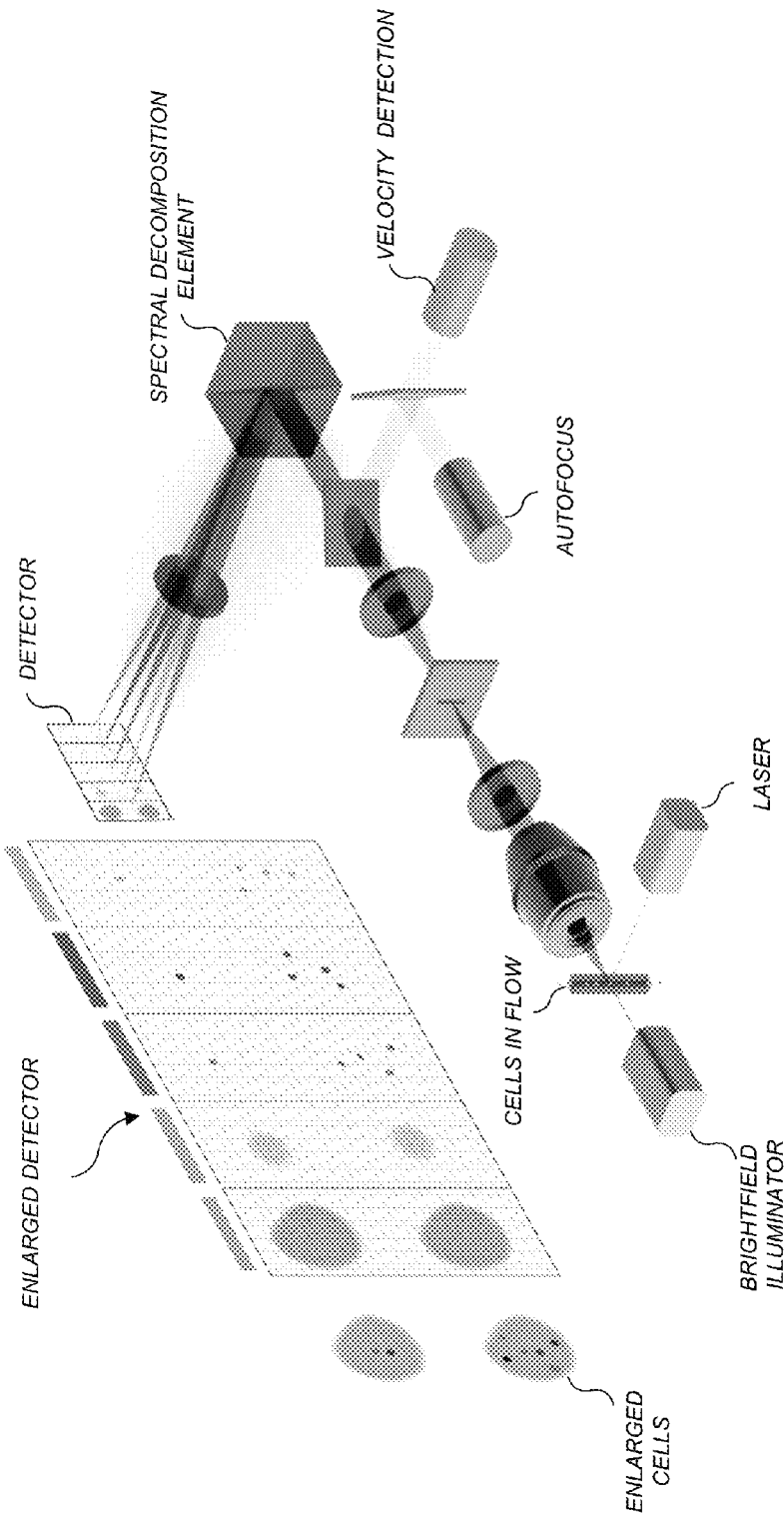
FIG. 1 shows a schematic representation of the ImageStream 100™ multispectral imaging cytometer.

By way of background, methodologies for simultaneous high speed multispectral imaging in brightfield, darkfield, and four channels of fluorescence of cells in flow were recently developed (see, e.g., U.S. Pat. Nos. 6,211,955 and 6,249,341). FIG. 1 illustrates an exemplary imaging system (e.g., the ImageStream platform). Cells are hydrodynamically focused into a core stream and orthogonally illuminated for both darkfield and fluorescence imaging. The cells are simultaneously trans-illuminated via a spectrally-limited source (e.g., filtered white light or a light emitting diode) for brightfield imaging. Light is collected from the cells with an imaging objective lens and is projected on a charge-coupled detector (CCD). The optical system has a numeric aperture of 0.75 and the CCD pixel size in object space is 0.5 microns square, allowing high resolution imaging at event rates of approximately 100 cells per second. Each pixel is digitized with 10 bits of intensity resolution, providing a minimum dynamic range of three decades per pixel. In practice, the spread of signals over multiple pixels results in an effective dynamic range that typically exceeds four decades per image. Additionally, the sensitivity of the CCD can be independently controlled for each multispectral image, resulting in a total of approximately six decades of dynamic range across all the images associated with an object.

Prior to projection on the CCD, the light is passed through a spectral decomposition optical system that directs different spectral bands to different lateral positions across the detector (see, e.g., U.S. Pat. No. 6,249,341). With this technique, an image is optically decomposed into a set of 6 sub-images, each corresponding to a different color component and spatially isolated from the remaining sub-images. This process allows for identification and quantitation of signals within the cell by physically separating on the detector signals that may originate from overlapping regions of the cell. Spectral decomposition also allows multimode imaging: the simultaneous detection of brightfield, darkfield, and multiple colors of fluorescence, as is exemplified in FIG. 1, which depicts a red brightfield illumination source and the associated transmitted light images in the red detector channel adjacent to fluorescent and scattered light images in the other spectral channels. The process of spectral decomposition occurs during the image formation process rather than via digital image processing of a conventional composite image.

The CCD may be operated using a technique called time-delay-integration (TDI), a specialized detector readout mode that preserves sensitivity and image quality even with fast relative movement between the detector and the objects being imaged. As with any CCD, image photons are converted to photocharges in an array of pixels. However, in TDI operation the photocharges are continuously shifted from pixel to pixel down the detector, parallel to the axis of flow. If the photocharge shift rate is synchronized with the velocity of the flowing cell's image, the effect is similar to physically panning a camera: image streaking is avoided despite signal integration times that are orders of magnitude longer than in conventional flow cytometry. For example, an instrument may operate at a continuous data rate of approximately 30 megapixels per second and integrate signals from each object for 10 milliseconds, allowing the detection of even faint fluorescent probes within cell images that are acquired at high-speed. Careful attention to pump and fluidic system design to achieve highly laminar, non-pulsatile flow eliminates any cell rotation or lateral translation on the time scale of the imaging process (see, e.g., U.S. Pat. No. 6,532,061).

A real-time algorithm analyzes every pixel read from the CCD to detect the presence of object images and calculate a number of basic morphometric and photometric features, which can be used as criteria for data storage. Data files encompassing 10,000-20,000 cells are typically about 100 MB in size and, therefore, can be stored and analyzed using standard personal computers. The TDI readout process operates continuously without any "dead time," which means every cell can be imaged and the coincidental imaging of two or more cells at a time, as depicted in FIG. 1, presents no barrier to data acquisition.

Such an imaging system can be employed to determine morphological, photometric, and spectral characteristics of cells and other objects by measuring optical signals, including light scatter, reflection, absorption, fluorescence, phosphorescence, luminescence, etc. As used herein, morphological parameters may be basic (e.g., cellular size, or nuclear shape) or may be complex (e.g., identifying cytoplasm size as the difference between cell size and nuclear size). As a further example, morphological parameters may include nuclear area or size, perimeter, texture or spatial frequency content, centroid position, shape (i.e., round, elliptical, barbell-shaped, etc.), volume, and ratios of any of these parameters. Morphological parameters may also include cytoplasm size, internal cell granularity, texture or spatial frequency content, volume and the like, of cells. As used herein, photometric measurements with the aforementioned imaging system can enable the determination of nuclear optical density, cytoplasm optical density, background optical density, and the ratios of any of these values. An object being imaged can be stimulated into fluorescence or phosphorescence to emit light, or may be luminescent, wherein light is produced by the object, without stimulation. In each case, the light from the object may be imaged on a TDI detector of the imaging system to determine the presence and amplitude of the emitted light, the number of discrete positions in a cell or other object from which the light signal(s) originate(s), the relative placement of the signal sources, and the color (wavelength or waveband) of the light emitted at each position in the object.

The present disclosure provides methods of using both photometric and morphometric features derived from multi-mode imagery of objects in flow. Such methods can be employed as a cell analyzer to determine one or more cell states or types, and cell features, in heterogeneous populations of cells when entrained in a fluid flowing through an imaging system. As used herein, cell states or types may include live cells, cells early or late in the process of dying (e.g., apoptotic cells or necrotic cells), cells propagating (e.g., cells in different phases of division), populations and sub-populations of cells (e.g., leucocyte subpopulations in blood), etc., and combinations thereof. However, it should also be understood that these exemplary methods might be used for imaging and distinguishing other moving objects that have identifiable photometric and morphometric features. As used herein, gating refers to a subset of data relating to photometric or morphometric imaging. For example, a gate may be a numerical or graphical boundary of a subset of data that can be used to define the characteristics of particles to be further analyzed. Here, gates have been defined, for example, as a plot boundary that encompasses viable (normal) cells as double negatives (DN gate), or early apoptotic cells as single positives (SP gate), or late apoptotic and necrotic cells as double positives (DP gate). Further, backgating may be a subset of the subset data. For example, a forward scatter versus a side scatter plot in combination with a histogram from an additional marker (e.g., HLA-class I-PE) may be used to backgate a subset (e.g., late apoptotic cells) within the initial subset (e.g., late apoptotic and necrotic cells).

In using an imaging system as described herein, it should be made clear that a separate light source is not required to produce an image of the object (cell), if the object is luminescent (i.e., if the object produces light). However, many of the applications of an imaging system as described herein will require that one or more light sources be used to provide light that is incident on the object being imaged. A person having ordinary skill in the art will know that the location of the light sources substantially affects the interaction of the incident light with the object and the kind of information that can be obtained from the images on a TDI detector.

In addition to imaging an object with the light that is incident on it, a light source can also be used to stimulate emission of light from the object. For example, a cell having been contacted with probe conjugated to a fluorochrome (e.g., such as FITC, PE, APC, Cy5, or Cy5.5) will fluoresce when excited by light, producing a corresponding characteristic emission spectra from any excited fluorochrome probe that can be imaged on a TDI detector. Light sources may alternatively be used for causing the excitation of fluorochrome probes on an object, enabling a TDI detector to image fluorescent spots produced by the probes on the TDI detector at different locations as a result of the spectral dispersion of the light from the object that is provided by prism. The disposition of these fluorescent spots on the TDI detector surface will depend upon their emission spectra and their location in the object.

Each light source may produce light that can either be coherent, non-coherent, broadband or narrowband light, depending upon the application of the imaging system desired. Thus, a tungsten filament light source can be used for applications in which a narrowband light source is not required. For applications such as stimulating the emission of fluorescence from probes, narrowband laser light is preferred, since it also enables a spectrally decomposed, non-distorted image of the object to be produced from light scattered by the object. This scattered light image will be separately resolved from the fluorescent spots produced on a TDI detector, so long as the emission spectra of any of the spots are at different wavelengths than the wavelength of the laser light. The light source can be either of the continuous wave (CW) or pulsed type, preferably a pulsed laser. If a pulsed type illumination source is employed, the extended integration period associated with TDI detection can allow the integration of signal from multiple pulses. Furthermore, it is not necessary for the light to be pulsed in synchronization with the TDI detector.

In the exemplary embodiments of the present technology, it is to be understood that relative movement exists between the object being imaged and the imaging system. In most cases, it will be more convenient to move the object than to move the imaging system. However, it is also contemplated that in some cases, the object may remain stationary and the imaging system move relative to it. As a further alternative, both the imaging system and the object may be in motion, which movement may be in different directions and/or at different rates.

In certain aspects, there is provided an exemplary method for identifying a specific cell, comprising directing incident light at a cell, using a detector to obtain a side scatter image, and using the spatial frequency content of the side scatter image to identify the specific cell. Within certain exemplary embodiments, the methods of the instant disclosure may be used to identify a specific cell subpopulation that is part of larger heterogeneous cell population. For example, the methods of this disclosure may be used to identify a normal cell, a cell undergoing apoptosis (including early and late stage apoptosis), and a cell undergoing necrosis. Alternatively, the methods of the instant disclosure may be used to identify cells at particular stages of replication (S phase, G phase, M phase, etc.). Thus, in a heterogeneous population of cells, the methods of the invention may be used to identify at least one apoptotic cell and at least one necrotic cell and at least one normal (viable) cell—if all such types are present. In addition, early stage and late stage apoptotic cells may be identified.

In another aspect, the instant disclosure provides a method for identifying a specific cell, comprising directing incident light at a cell, using a detector to obtain a brightfield image, and using the spatial frequency content of the brightfield image to identify the specific cell. In certain embodiments, the spatial frequency content analyzed is of the nucleus. Any of the aforementioned exemplary embodiments may be used within the context of this aspect of the present technology.

In a further aspect, the instant disclosure provides a method for identifying a specific cell, comprising contacting a cell with a nuclear marker, directing incident light at the marked cell, using a detector to obtain an image of the cell, and using the nuclear marker image in combination with the spatial frequency content of the cell image to identify a specific cell. The marker used can be a fluorescence stain or dye. Again, any of the previous embodiments may be used within this method. In certain exemplary embodiments, only a single nuclear marker is used, such as 7-AAD.

In any of the aforementioned methods, multiple images may be collected simultaneously. Furthermore, in any of the aforementioned methods, there is relative motion between the cell and the detector. In addition, in any of the aforementioned methods, the detector is a time delay integration (TDI) charge-coupled detector.

The instant disclosure also provides a kit for use in a multispectral imaging system to identify a specific cell type, comprising a single nuclear marker, wherein a cell contacted with the single marker for a time sufficient to allow identification of an apoptotic cell or a necrotic cell with the multispectral imaging system, as described herein.

All of the U.S. patents, U.S. patent application publications, U.S. patent applications, foreign patents, foreign patent applications and non-patent publications referred to in this specification and/or listed in the Application Data Sheet, are hereby incorporated herein by reference, in their entirety. The present novel approach having been described, the following examples are intended to illustrate, and not limit, the scope of this technology.

EXAMPLES

Example 1

Induction of Apoptosis

Human acute T leukemic Jurkat cell line was obtained from ATCC (Rockville, Md.; catalog number CRL-1990) and maintained in RPMI 1640 (Gibco, Grand Island, N.Y.) containing 5% fetal bovine serum, 1 mM sodium pyruvate (Mediatech, Herndon, Va.), 100 .mu.M nonessential amino acids, 100 U/ml penicillin, 100 .mu.g/ml streptomycin, and 2 mM L-glutamine (BioWhittaker, Walkersville, Md.) in 5% $CO_2$ atmosphere at 37° C. The density of exponentially growing cells was less than $3 \times 10^5$ cells per ml at the time of all treatments. To induce apoptosis, cells were treated for 18 hours with 1 μM camptothecin (CPT, Sigma), a DNA topoisomerase I inhibitor.

Example 2

Induction of Necrosis

Human acute T leukemic Jurkat cell line was obtained from ATCC (Rockville, Md.; catalog number CRL-1990) and maintained in RPMI 1640 (Gibco, Grand Island, N.Y.) containing 5% fetal bovine serum, 1 mM sodium pyruvate (Mediatech, Herndon, Va.), 100 μM nonessential amino acids, 100 U/ml penicillin, 100 μg/ml streptomycin, and 2 mM L-glutamine (BioWhittaker, Walkersville, Md.) in 5% $CO_2$ atmosphere at 37° C. The density of exponentially growing cells was less than $3 \times 10^5$ cells per ml at the time of all treatments. To induce necrosis, cells were treated for 1 hour with 0.3% hydrogen peroxide (Sigma, St. Louis, Mo.).

Example 3

Staining to Identify Apoptotic Cells and Necrotic Cells

Control (untreated) cells, CPT treated (apoptotic) cells, and peroxide treated (necrotic) cells were independently counted and washed once in phosphate buffered saline (PBS, Fair Lawn, N.J.). Each cell group was resuspended at $10^7$ cells/ml in annexin V Binding Buffer (BD Pharmingen, San Diego, Calif.) containing Alexa Fluor 488 annexin V (Molecular Probes, Eugene, Oreg.) and 10 .mu.M 7-aminoactinomycin D (7-AAD, Molecular Probes), which serves as a nucleic acid-binding dye, for 10 minutes at room temperature. Necrotic cells were additionally stained with phycoerythrin (PE)-labeled anti-HLA-A, B, C (clone G46-2.6, BD Pharmingen; anti-HLA class I). Each cell group was washed in annexin V Binding Buffer, fixed in 2% paraformaldehyde (Sigma), and analyzed as either single populations or as a mixture by flow cytometry and immunofluorescence microscopy.

Example 4

Conventional Flow Cytometry and Imaging Flow Cytometry

For flow cytometry, cell fluorescence data excited by a 488 nm laser were acquired using the FACSort™ cytometer (BD Immunocytometry Systems, San Jose, Calif.) and analyzed using CellQuest™ (BD Immunocytometry Systems). For imaging flow cytometry, fixed cells at 5×10$^7$ cells per ml were run at 100 cells per second on an ImageStream100™ ("Beta" version), and the data analyzed using the ImageStream Data Analysis and Exploration Software™ (IDEAS™).

Example 5

Instrumentation for Multispectral Imaging Flow Cytometry

FIG. 1 provides an exemplary layout of the ImageStream™ platform. Cells are hydrodynamically focused into a core stream and orthogonally illuminated for both darkfield and fluorescence imaging. The cells are simultaneously trans-illuminated via a spectrally-limited source (e.g., with filtered white light or with light from a light emitting diode) for brightfield imaging. Light is collected from the cells with an imaging objective lens and is projected onto a charge-coupled detector (CCD). The optical system has a numeric aperture of 0.75 and the CCD pixel size in object space is 0.5 microns square, enabling high resolution imaging at event rates of approximately 100 cells per second. Each pixel is digitized with 10 bits of intensity resolution, providing a minimum dynamic range of three decades per pixel. In practice, the spread of signals over multiple pixels results in an effective dynamic range that typically exceeds four decades per image. Additionally, the sensitivity of the CCD can be independently controlled for each multispectral image, resulting in a total of approximately six decades of dynamic range across all the images associated with an object.

Prior to projection on the CCD, the light is passed through a spectral decomposition optical system that directs different spectral bands to different lateral positions across the detector (see, e.g., U.S. Pat. No. 6,249,341). With this technique, an image is optically decomposed into a set of 6 sub-images, each corresponding to a different color component and spatially isolated from the remaining sub-images. This is exemplified in FIG. 1, which depicts a red brightfield illumination source and the associated transmitted light images in the red detector channel adjacent to fluorescent and scattered light images in the other spectral channels. The process of spectral decomposition occurs during the image formation process rather than via digital image processing of a conventional composite image.

The CCD is operated using time-delay-integration (TDI), in which image photons converted to photocharges in an array of pixels are continuously shifted (at a rate synchronized with the velocity of the flowing cell's image) from pixel to pixel down the detector and parallel to the axis of flow to avoid image streaking. For example, the instrument can operate at a continuous data rate of approximately 30 megapixels per second and integrate a signal from each object for 10 milliseconds, which enables the detection of even faint fluorescent probes within cell images that are acquired at high speed. Attention to pump and fluidic system design to achieve highly laminar, non-pulsatile flow can eliminate cell rotation or lateral translation on the time scale of the imaging process (see, e.g., U.S. Pat. No. 6,532,061). Every pixel read from the CCD is analyzed by a real-time algorithm that detects the presence of object images and calculates a number of basic morphometric and photometric features, which can be used as criteria for data storage. Data files encompassing 10,000-20,000 cells can be about 100 MB in size, and are stored and analyzed using standard personal computers.

Example 6

Immunofluorescence Microscopy

Fixed control and treated cells were placed on a conventional glass slide (Erie Scientific, Portsmouth, N.H.), mixed 1:1 with Antifade (Molecular Probes) and covered with a cover slip. The cells were visualized at 400× using an Eclipse E600 (Nikon, Melville, N.Y.) fluorescence microscope equipped with filters appropriate for Alexa Fluor 488 (535/40 nm emission) and 7-AAD (630/60 nm emission).

Example 7

Conventional Analysis of Cells Induced to Undergo Apoptosis or Necrosis

Jurkat T cells were treated with peroxide (to induce necrosis), CPT (to induce apoptosis, which contained cells in both early and late stages of apoptosis), or were untreated (control). The three cell populations were then stained with Alexa Fluor 488 annexin V and 7-AAD and evaluated by brightfield, darkfield, and fluorescence microscopy, and by conventional flow cytometry (FIG. 2). As an alternative to 7-AAD, one of 4',6-diamidino-2-phenylindole (DAPI), Hoechst 33342, Hoechst 33258, propidium iodide, or other examples of nuclear or DNA-specific dyes can be used. The vast majority (>98%) of the control cells were viable at the time of staining, and were annexin V$^-$, 7-AAD$^-$ (double negative, DN; FIG. 2A). CPT-treated (apoptotic) cells had two populations of cells, those that were annexin V$^+$ (single positive, SP, or early apoptotic cells), and those that were annexin V$^+$, 7-AAD$^+$ (double positive, DP, or late apoptotic cells) (FIG. 2B). Similar to late apoptotic cells, peroxide-treated (necrotic cells) also stained positively with both annexin V and 7-AAD (FIG. 2C). However, the condensed, fragmented nuclei of late apoptotic cells could be easily distinguished from the intact nuclei of necrotic cells by immunofluorescence microscopy. In addition, apoptotic cells exhibited greater darkfield intensity and texture as compared to necrotic cells (see B and C image panels on right, respectively).

Example 8

Analysis of Heterogeneous Cell Population Normal, Apoptotic and Necrotic

A mixture of control, apoptotic, and necrotic Jurkat cells (individually prepared as described in Examples 1 and 2) were analyzed in parallel by conventional flow cytometry and on an ImageStream 100™ (Beta system, multispectral imaging flow cytometer). In this experiment, all cells were stained with Alexa Fluor 488-conjugated annexin V and 7-AAD. Alternatively, as noted in the previous Example, instead of staining with 7-AAD, the cells could have been stained with one of 4',6-diamidino-2-phenylindole (DAPI), Hoechst 33342, Hoechst 33258, propidium iodide, or other examples of nuclear or DNA-specific dyes. Necrotic cells were also stained with PE-conjugated anti-HLA class I before mixing the cell populations to aid in distinguishing necrotic cells from late stage apoptotic cells, and to permit "backgating" when necessary. On the ImageStream™, each cell was simultaneously imaged in darkfield (488 nm laser side scatter), green fluorescence (500-550 nm, annexin V channel), orange fluorescence (550-600 nm, PE channel), red fluorescence (600-650 nm, 7-AAD channel), and brightfield (660-720 nm). Cells were grouped into live (DN), early apoptotic (SP), or double positive (DP, which would include late apoptotic and necrotic cells) populations based on the total intensities of annexin V and 7-AAD staining.

Figure 3A:
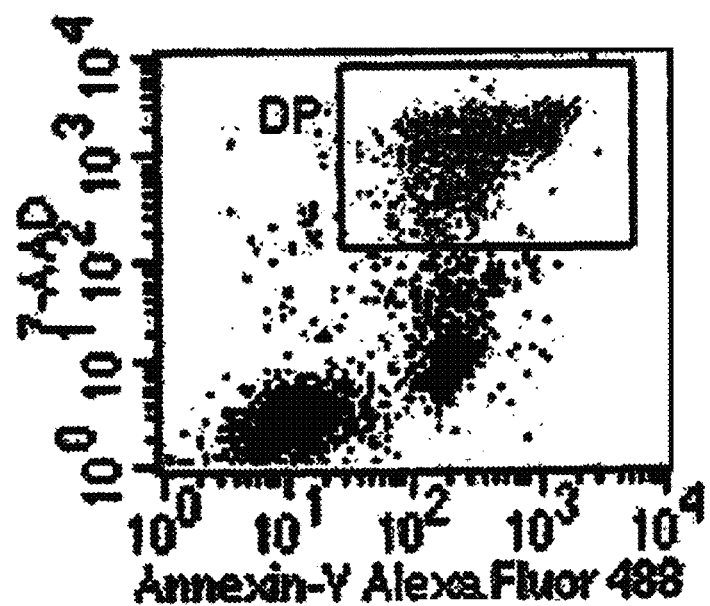
FIGS. 3A-3E show flow cytometric imaging of untreated, CPT-treated and peroxide-treated Jurkat cells that were stained with Alexa Fluor 488 conjugated annexin V and 7-AAD. Peroxide-treated cells were also separately stained with HLA class I-PE. After staining, equal cell numbers of the three populations of cells were mixed and analyzed by (A) conventional flow cytometry using a FACSort™; and (B) multispectral imaging of cells in flow using an ImageStream 100™ cytometer. The six channel images of cells from representative members of the double positive (DP), single positive (SP), and double negative (DN) populations identified using the ImageStream 100™ are shown in panels C, D, and E, respectively.
Figure 3B:
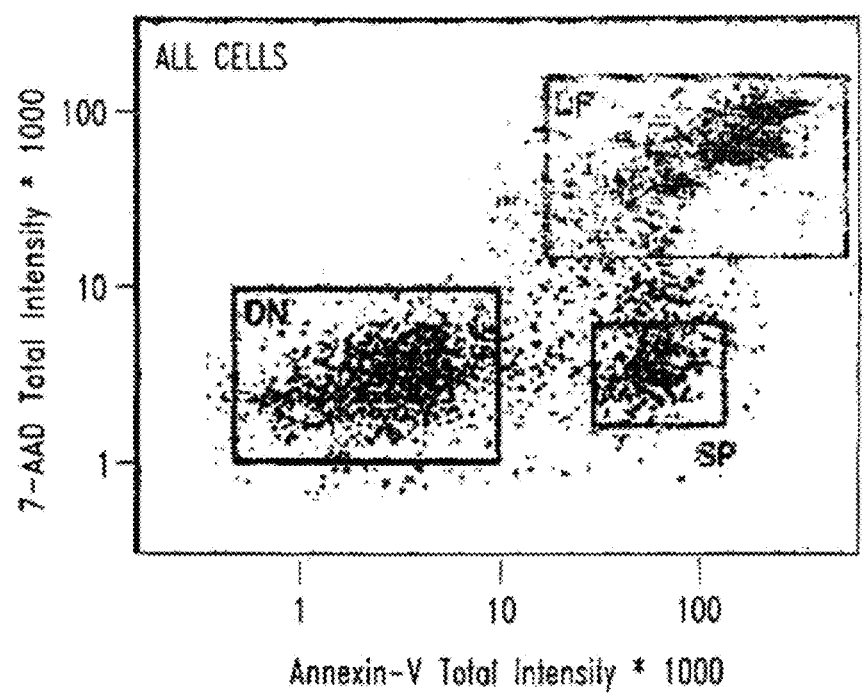
Figure 3C:
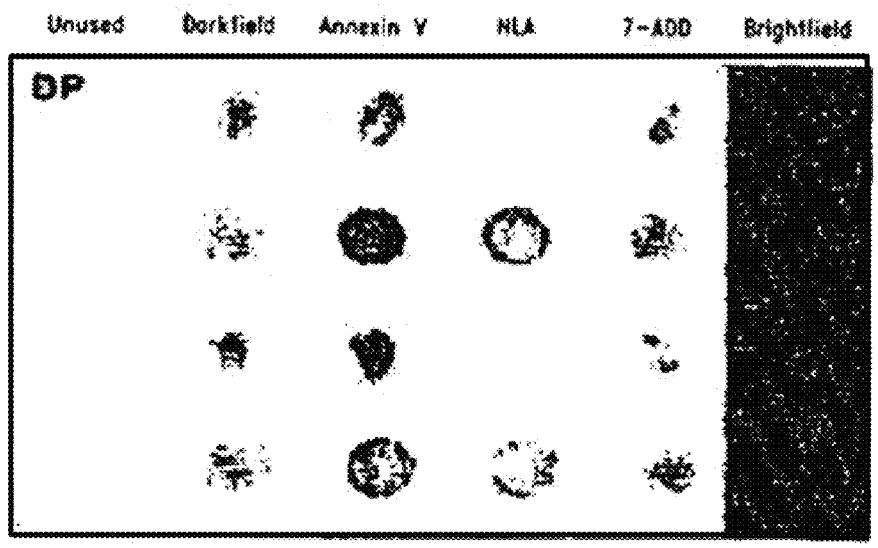
Figure 3D:
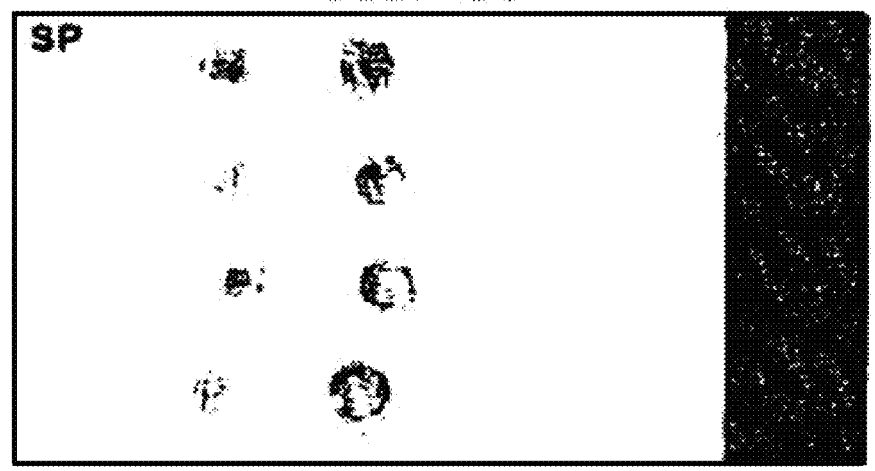
Figure 3E:
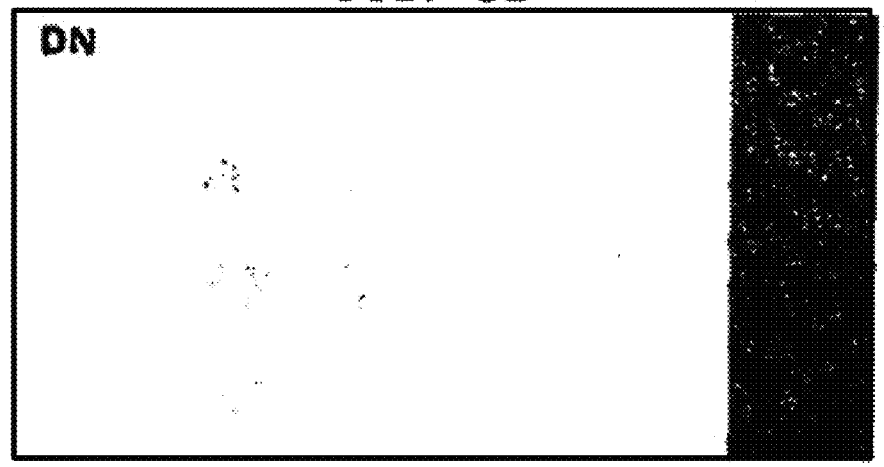

Similar bivariate dot-plots of annexin V and 7-AAD staining were obtained in analyses from both the conventional flow cytometer (see FIG. 3A) and the multispectral imaging flow cytometer (see FIG. 3B). However, a unique aspect of data collected on the ImageStream™ is that each data point can be "clicked on" to observe the cell imagery associated with each data point. Consequently, each population gate can be used to perform a "virtual cell sort" by displaying individual images of cells that fall within each gate—for example, representative images of cells contained in the DP, SP and DN gates can be "virtually sorted," as shown in FIGS. 3C, 3D and 3E, respectively, with each image row representing a different cell. Early apoptotic cells (cells in the SP gate) appear slightly shrunken, with more complex brightfield and darkfield morphologies, as compared to live cells in the DN gate. The double positive (DP) population contains cells with two distinct morphologies—one containing small, irregularly shaped cells with condensed, fragmented nuclei; and a second containing larger cells with large, unfragmented nuclei that stained uniformly with 7-AAD. The morphology of these two populations of cells is consistent with cells in the late stage of apoptosis and necrosis, respectively. Thus, in the absence of imagery provided by the multispectral imaging flow cytometer, data obtained from a conventional flow cytometer does not permit discrimination of similarly stained cells, such as late apoptotic cells from necrotic cells.

Example 9

Conventional Methods to Distinguish Late Apoptotic and Necrotic Cells

Figure 4A:
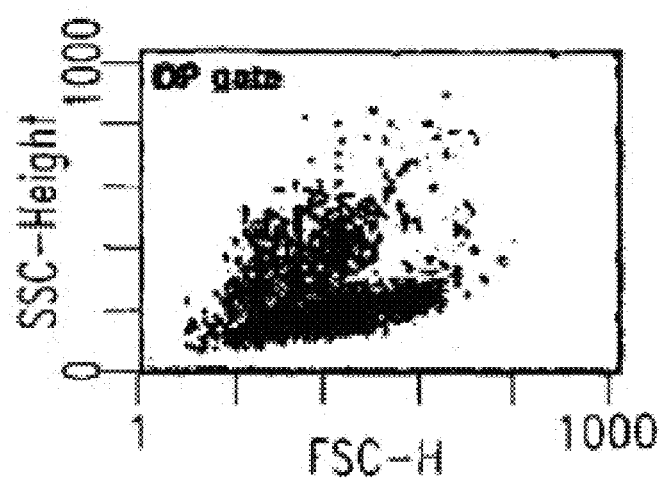
FIGS. 4A-4F show (A) a laser scatter analysis (forward scatter vs. side scatter) of the "Dgate" population of cells from FIG. 3A, by way of CellQuest™ software on data obtained from a FACSort™ cytometer; (B) a single color histogram of HLA class I-PE on DP cells from FIG. 3A as measured using a FACSort™ cytometer; (C) backgating of HLA class I-PE+ cells from FIG. 4B onto the scatter histogram of FIG. 4A, wherein HLA class I-PE+ cells (i.e., peroxide-treated, necrotic) are shown in red and HLA class I-PE− cells (i.e., CPT-treated, apoptotic) are shown in blue; (D) a bivariate plot (scatter histogram) of the "Brightfield Area" vs. the "488 nm Scatter Peak Intensity" produced using IDEAS™ software on data obtained using the ImageStream™ cytometer; (E) a single color histogram of HLA class I-PE on DP cells from FIG. 3D as measured using the ImageStream cytometer; (F) backgating of HLA class I-PE+ cells from FIG. 4E onto the scatter histogram of FIG. 4D, wherein HLA class I-PE+ cells (i.e., peroxide-treated, necrotic) are shown in red and HLA class I-PE− cells (i.e., CPT-treated, apoptotic) are shown in yellow.
Figure 4B:
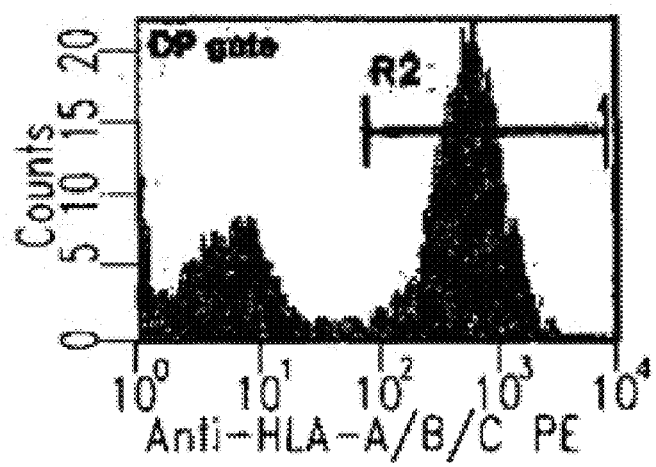
Figure 4C:
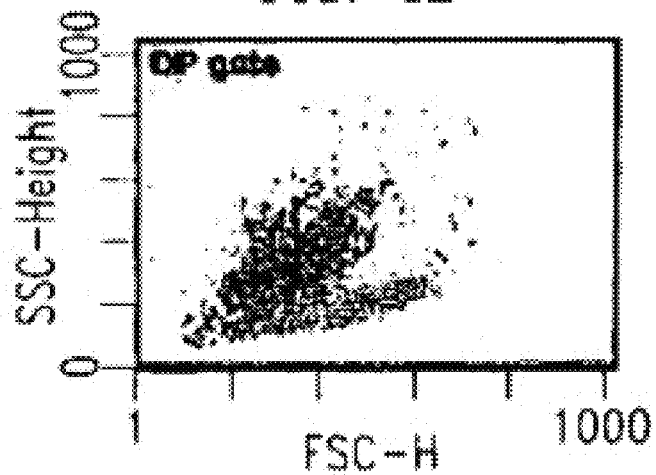

As noted in Example 8, although advanced apoptotic and necrotic cells differ morphologically, they cannot be distinguished based solely on annexin V and 7-AAD fluorescence. Plotting the mixed late apoptotic and necrotic DP population on a forward scatter vs. side scatter (FSC vs. SSC) plot reveals two distinct populations of cells (see FIG. 4A). Analysis of the DP population of cells obtained on the conventional flow cytometer for staining with PE (which was used to stain only the necrotic subpopulation of cells) permits separation of the necrotic and apoptotic subpopulations of cells (FIG. 4B). Backgating the PE positive necrotic population in blue reveals that the low SSC population consists of necrotic cells (FIG. 4C). However, without the aid of an extra marker (in this case, anti-HLA class I-PE) or imagery as described in Example 8, data obtained from a conventional flow cytometer does not permit discrimination of similarly stained cells, such as late apoptotic cells from necrotic cells.

Example 10

Multispectral Identification of Late Apoptotic and Necrotic Cells

Figure 4D:
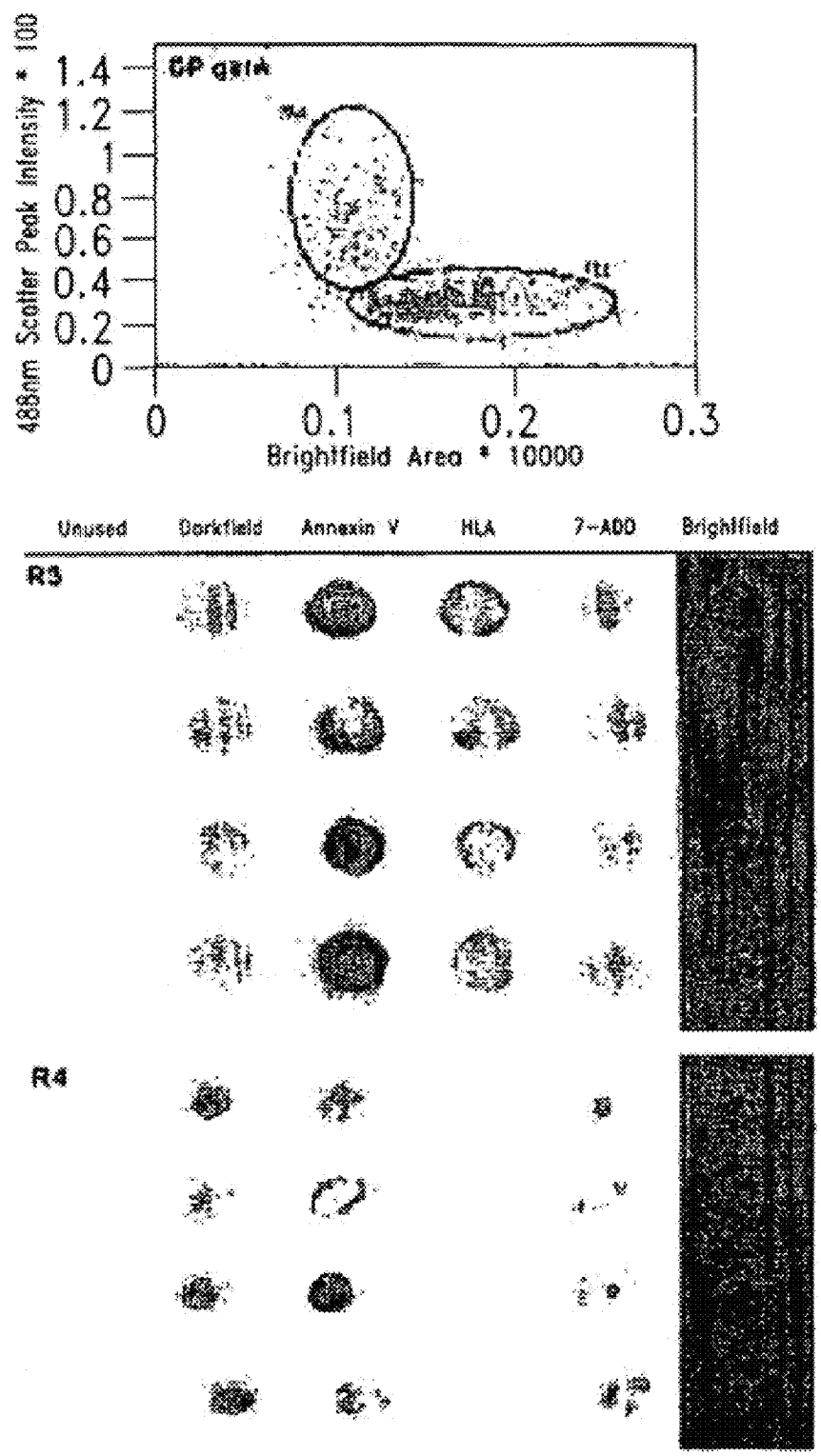
Figure 4E:
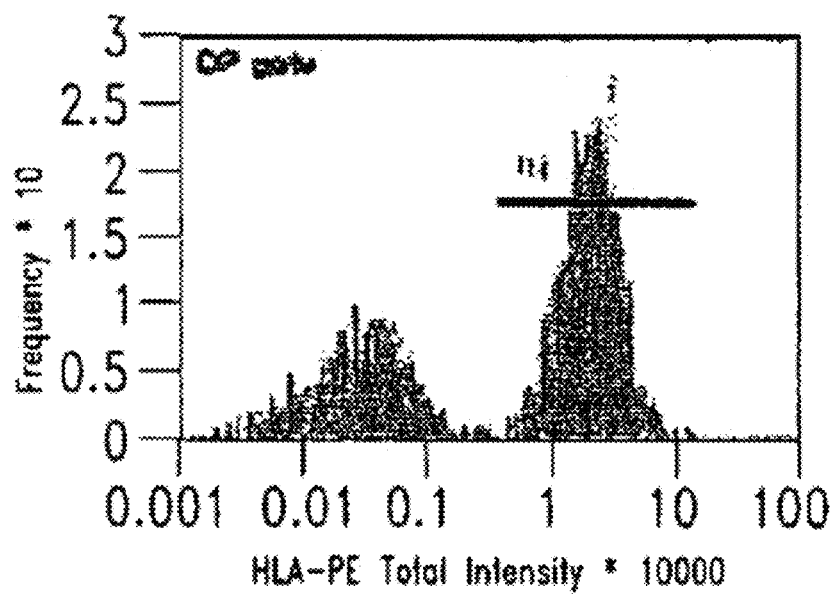
Figure 4F:
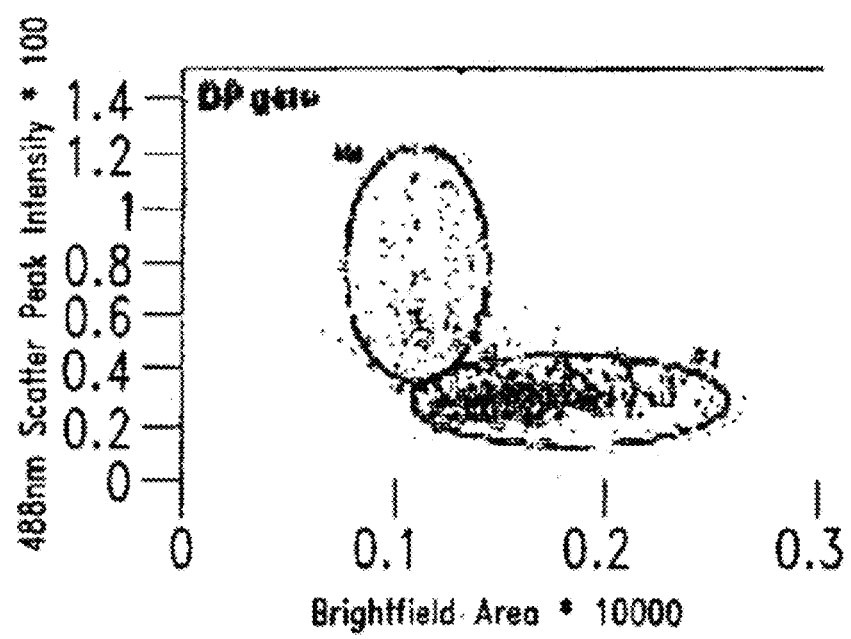

Analysis of the DP population with IDEAS™ software for size (Brightfield Area) and Scatter Peak Intensity also revealed two populations of cells (FIG. 4D). The nuclei of cells that fell within the high brightfield area, low scatter peak intensity area (R3) were intact, uniformly stained with 7-AAD, and had a morphology consistent with necrotic cells. The nuclei of cells that fell within the low brightfield area, high scatter peak intensity area (R4) were condensed and fragmented, and had a morphology consistent with cells in the late stages of apoptosis. Backgating PE$^+$ cells (identified in the histogram shown in FIG. 4E) in yellow verified that R3 gated cells were derived from the necrotic treatment group (FIG. 4F). This conclusion is further supported by morphologic examination of cells in the image galleries of the R3 and R4 gated cells, and confirms that the low area/high texture cells were apoptotic (HLA-class I PE$^+$ cells containing fragmented 7-AAD staining nuclei; lower right gallery) while high area/low texture cells were necrotic (HLA class I-PE$^+$ cells containing uniform 7-AAD staining nuclei; upper right gallery). Thus, the data obtained from multispectral imaging is provided in a form that allows one to distinguish similarly stained cells, such as late apoptotic cells from necrotic cells.

It is again noted that instead of using 7-AAD, other fluorescence stains can be employed as a stain or dye for marking a nucleus. For example, 4',6-diamidino-2-phenylindole (DAPI), Hoechst 33342, Hoechst 33258, and propidium iodide can be used as a fluorescence stain.

Example 11

Complex Morphologic Feature Identity Using Multispectral Imaging

Multispectral image data collection not only enables calculation of standard intensity-based parameters and statistics employed in conventional flow cytometry, but also permits quantitation of numerous other morphologic features (e.g., cell area, perimeter, aspect ratio, texture, spot counts, cell centroid, gradient intensity, spatial frequency). Using this capability, it is possible to distinguish all four cell populations (i.e., live, early apoptotic, late apoptotic and necrotic cells) in a single step using morphologic features derived from 7-AAD, brightfield and darkfield imagery (and in the absence of other staining procedures often used) to "identify" apoptotic cells.

The complexity of nuclear, brightfield and darkfield morphologies can be used for visually sorting the cells. For example, by subtracting the 7-AAD image area (nuclear size) from the Brightfield area (cell size), a value is obtained that is an indication of cytoplasmic size. When this complex morphologic feature (herein referred to as "Brightfield 7-AAD Area") was used in conjunction with a feature derived from darkfield imagery (i.e., 488 nm spatial scatter frequency, which is an indication of internal cell complexity or cell granularity), four subpopulations of cells became evident (see FIG. 5). The 488 nm spatial scatter frequency can be calculated by computing the standard deviation of the individual pixel intensities within the segmented dark field image mask.

Live cells (depicted in blue, FIG. 5, center panel) excluded the cell-impermeant 7-AAD fluorescent DNA binding dye, which minimized the nuclear image area and resulted in cells with a large calculated cytoplasmic area.

Early apoptotic cells (depicted in green, FIG. 5, center panel) are just as effective as live cells at excluding 7-AAD, but their total brightfield area is slightly smaller due to the early stages of cytoplasmic blebbing, thereby resulting in an intermediate value for the "Brightfield-7AAD Area" parameter. Also associated with the early stages of apoptosis is a significant increase in 488 nm scatter peak intensity, which clearly separates these cells from live cells on the vertical axis of the dot-plot.

Necrotic cells (depicted in yellow, FIG. 5, center panel) and late apoptotic cells (depicted in red, FIG. 5, center panel) both had compromised membrane integrity, which permits free entry of 7-AAD and thus strong nuclear images of relatively large area, shifting these populations to the left on the dot-plot. However, these two cell populations can be clearly separated based on the peak intensity measurements derived from their 488 nm scatter parameters. Necrotic cells produce darkfield images of relatively low complexity compared to the more complex and heterogeneous darkfield images of late apoptotic cells, thus clearly separating the two populations in the vertical axis.

Figure 5:
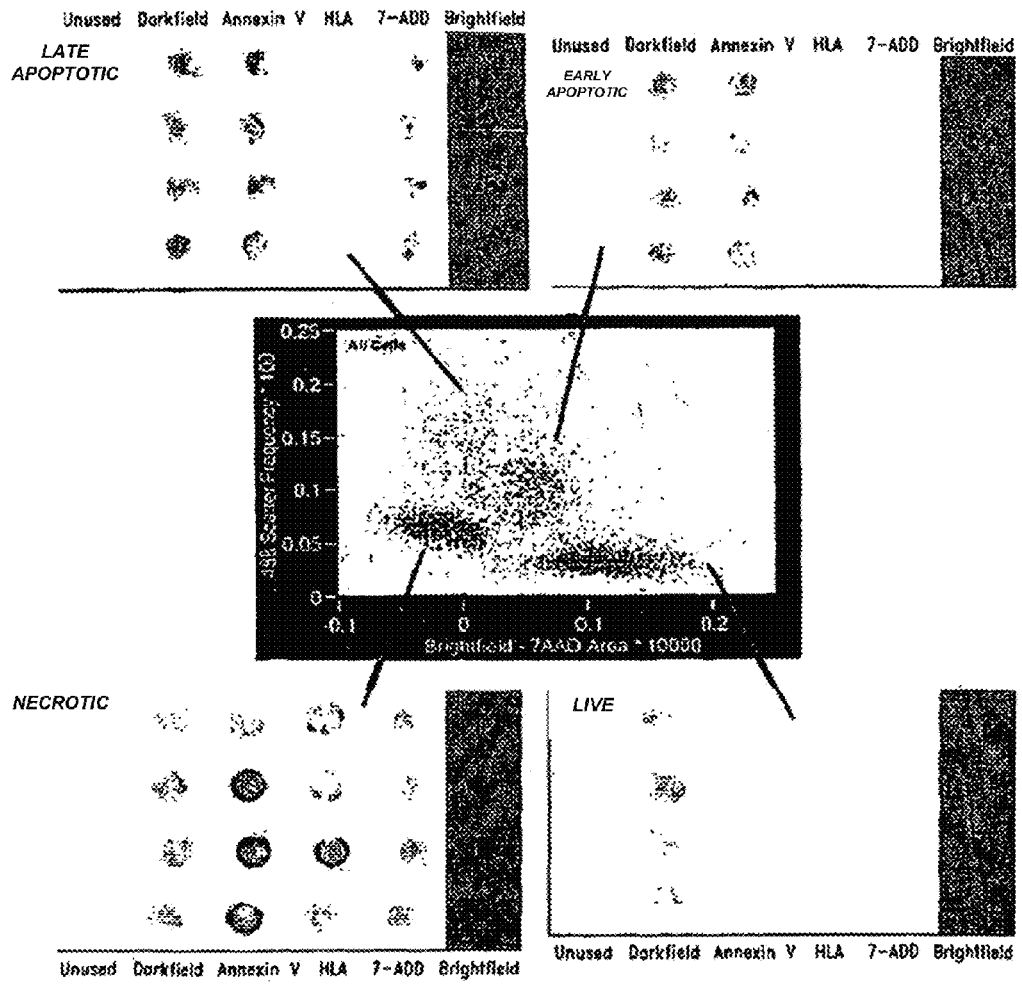
FIG. 5 shows resolution of live, early and late apoptotic, and necrotic cells using morphometric features based on scatter intensity, brightfield area, and nuclear area. Backgating of the four cell populations that had been identified using alternative criteria confirmed their identity as live cells and early apoptotic cells with the DN and SP cells, respectively, shown in FIG. 3B (shown in blue and green, center panel), and as necrotic and late apoptotic cells with cells contained in gates R3 and R4, respectively, shown in FIG. 4 (shown in yellow and red, center panel).

Inspection of the associated image galleries associated with these four gated populations of cells confirmed the classification of each population (see FIG. 5, upper and lower panels).

From the foregoing it will be appreciated that, although specific exemplary embodiments of the present novel approach have been described herein for purposes of illustration, various modifications may be made without deviating from the spirit and scope of the invention. Accordingly, the invention is not limited except as by the appended claims.

The invention in which an exclusive right is claimed is defined by the following:

1. A method for identifying a specific cell as being of a known cell type, wherein the known cell type relates to the viability of the cell, comprising:
    staining a nucleus of the specific cell with a fluorescence stain;
    directing incident light at the specific cell to obtain a nuclear image and a brightfield image of the specific cell with a light detector; and
    determining the known cell type to which the specific cell corresponds, based on morphologic features of the specific cell that are derived from the nuclear image and the brightfield image, wherein the morphologic features include at least one morphologic feature selected from the group consisting of a size of the specific cell, a size of a nucleus in the specific cell, and a brightfield image contrast of the specific cell.

2. The method of claim 1, wherein the specific cell is stained with a nucleic acid-binding dye consisting of one of 7-aminoactinomycin D (7-AAD) or propidium iodide.

3. The method of claim 1, wherein there is relative motion between the specific cell and the detector.

4. The method of claim 1, wherein the specific cell identified is contained within a heterogeneous cell population, and the nuclear image and the brightfield image are collected for the specific cell from nuclear images and brightfield images of the heterogeneous cell population.

5. The method of claim 1, wherein the specific cell identified is an apoptotic cell.

6. The method of claim 5, wherein the apoptotic cell is an early stage apoptotic cell or a late stage apoptotic cell.

7. The method of claim 1, wherein the specific cell identified is a necrotic cell.

8. The method of claim 1, wherein the specific cell identified is at least one of an apoptotic cell and a necrotic cell.

9. A method for identifying a specific cell, to enable a determination to be made as to whether the specific cell corresponds to a known cell type, wherein the known cell type relates to the viability of the cell, comprising:
    directing incident light at the specific cell and using a detector to image the specific cell;
    calculating a contrast metric for a brightfield image of the specific cell;
    determining a nuclear size for the specific cell from nuclear imagery of the specific cell; and
    based upon the contrast metric for the brightfield image and on the nuclear size of the specific cell, determining if the specific cell corresponds to the known cell type.

10. The method of claim 9, wherein there is relative motion between the specific cell and the detector.

11. The method of claim 9, wherein the specific cell identified is contained within a heterogeneous cell population, and images are produced for the heterogeneous cell population.

12. The method of claim 9, wherein the specific cell is identified as an apoptotic cell.

13. The method of claim 12, wherein the apoptotic cell is an early stage apoptotic cell or a late stage apoptotic cell.

14. The method of claim 9, wherein the specific cell identified as a necrotic cell.

15. The method of claim 9, wherein the specific cell identified is as at least one of an apoptotic cell and a necrotic cell.

* * * * *